United States Patent [19]
Desai

[11] Patent Number: 4,944,918
[45] Date of Patent: Jul. 31, 1990

[54] STERILIZATION OF BLOOD COMPONENT SEPARATION DEVICES

[75] Inventor: Jay S. Desai, Closter, N.J.

[73] Assignee: Becton, Dickinson and Company, Franklin Lakes, N.J.

[21] Appl. No.: 144,214

[22] Filed: Jan. 15, 1988

[51] Int. Cl.$^5$ .......................... A61L 2/08; G01N 1/00
[52] U.S. Cl. ........................ 422/22; 422/99; 422/102; 436/177
[58] Field of Search .......................... 422/99, 102, 22; 436/177; 210/748, 787

[56] References Cited

U.S. PATENT DOCUMENTS

| | | | |
|---|---|---|---|
| 2,188,371 | 1/1940 | Merriam | 422/26 X |
| 2,250,474 | 7/1941 | Eisenbrand et al. | 422/1 X |
| 3,920,549 | 11/1975 | Gigliello et al. | |
| 4,101,422 | 7/1978 | Lamont et al. | |
| 4,190,535 | 2/1980 | Luderer et al. | |
| 4,235,725 | 11/1980 | Semersky | 422/22 X |
| 4,695,460 | 9/1987 | Holme | 424/101 |
| 4,778,766 | 10/1988 | Tanaka et al. | 436/63 |

OTHER PUBLICATIONS

"The Merck Index" 10th ed., Merck & Co., Inc., 1983 p. 433.
"Lange's Handbook of Chemistry" 13th ed., Dean, J. A., 1985, p. 7-666.
"Rapid, Quantitative Human Lymphocyte Separation and Purification in a Closed system", *Molecular Immunology*, 1979, vol. 16, pp. 621-624-A. A. Luderer, A. R. Zine, D. M. Hess, J. N. Henyan and G. Odstrchel.

*Primary Examiner*—Robert J. Warden
*Assistant Examiner*—Jeffrey R. Snay
*Attorney, Agent, or Firm*—Robert P. Grindle

[57] ABSTRACT

A method of sterilization is provided and a sterilized product from the method for blood separation tubes utilizing a density gradient medium comprised of ficoll and sodium diatrizoate alone or in combination with other such mediums by exposing such mediums to radiation sterilization from such sources as Cobalt 60 without any precipitation out of the components of the medium. This is achieved by the addition of a buffer to the gradient medium at a rate which will provide a specific pH level for the medium after exposure.

10 Claims, 1 Drawing Sheet

STERILIZATION OF BLOOD COMPONENT SEPARATION DEVICES

BACKGROUND AND STATEMENT OF THE INVENTION

Generally speaking, this invention relates to assemblies for separating blood serum or plasma from the cellular portion of a blood sample. More particularly, this invention relates to a method for sterilizing the assembly by the use of radiation sterilization.

Separation assemblies of the kind discussed herein typically include an elongated glass tube of varying design and containing the blood sample, with the tube being subjected, once the sample is introduced into the tube, to centrifugation until the cellular portion (heavy phase) and serum or plasma (light phase) are completely separated. To maintain separation after centrifuging and to facilitate decanting or removal of the light phase by pipette, a barrier means is provided within the assembly between the phases. It is to this barrier means in particular that the invention herein is directed.

For example, thixotropic gels have been utilized as a barrier medium for such assemblies with the gels responding to centrifugal forces during centrifugation to move into a position separating the heavier and lighter phases of a sample under consideration. Moreover, newtonian gels have been used instead of thixotropic gels. Also, a density gradient medium, namely sucrose/epichlorohydrin polymer with sodium diatrizoate (ficoll-hypaque) has been used alone or in combination with the above-noted gels. Other such products include iodine containing contrast mediums such as NYCODENZTM TM, owned by Nyegaard & Co., A/S (Norway Joint Stock Company), Oslo 4, Norway. One well-known ficoll-hypaque product is HISTOPAQUER ® a product of Sigma Chemical Co., 3050 Spruce Street, St. Louis, Mo. 63103, while another is FICOLL-PAQUER ® a product of Pharmacia Fine Chemicals AB, Uppsala, Sweden.

At any rate, when it was discovered that ficoll-hypaque could be used with a newtonian or thixotropic gel to have an improved product over either one of these materials separately, the product was presterilized by autoclaving. Alternatively, the ficoll-hypaque may be sterilized by filter sterilization through a, for example, 0.22 micron pore size filter. Both autoclaving and filtering are approaches which accomplish proper sterilization. However, these procedures are somewhat difficult to handle in the sense of manufacturing many thousands of these blood separation tube assemblies in a production line. It is far more convenient, for example, to utilize radiation sterilization which can be imparted in the production line without any separate stage or application as is required for filtering or autoclaving.

It has been found, however, that with the use of ficoll-hypaque in any of the combinations discussed above for blood separation tube assemblies, that a portion of the ficoll-hypaque component precipitates out upon exposure to, for example, Cobalt 60 radiation. Thus, it has been standard procedure to utilize the filtration form of sterilization discussed above, or autoclaving even with the problems noted.

By contrast, it has now been found, with this invention, that radiation sterilization can be used with such tube assemblies, including a ficoll-hypaque product in combination, for example, with a thixotropic gel by the addition of sodium bicarbonate or other buffering material for the density gradient medium component in order to establish a particular pH level after exposure. When this is done, no precipitation takes place. Radiation sterilization is appropriate, therefore, in a production line, in accordance with this invention, for producing tube assemblies of the kind discussed above.

For example, as one specific arrangement of tube assembly, in accordance with this invention, a conventional glass tube may be selected and a thixotropic gel introduced into and adjacent the closed end of the tube. Subsequently, a HISTOPAQUER ® material is introduced on top of the thixotropic gel. In this connection, the HISTOPAQUER ® is, as discussed above, a sucrose/epichlorohydrin polymer with sodium diatrizoate. The sodium bicarbonate buffer is introduced as a 0.1-0.5 percent solution by volume which provides a range of between about 6.5-7.6 pH after radiation exposure.

In considering generally the conditions for carrying out this invention, the buffer may include, for example, sodium bicarbonate or sodium carbonate alone or in combination with potassium or sodium-mono or dibasic phosphates. Another example of buffer which may be utilized, in accordance with this invention, is tris-hydroxymethyl amino methane (TRIS) with or without sodium or potassium phosphate or hydroxyethyl piperazine/N/2/ethane sulfonic acid (HEPES) with or without sodium or potassium phosphate. Phosphate buffers are especially useful for eliminating undesirable pH shifts before and after the sterilization procedure herein because they stabilize the other organic or inorganic buffers present.

It should be borne in mind that when certain of these buffers are selected, in accordance with the invention, the ficoll-hypaque solutions may have to be adjusted at a higher pH of, for example, about 8.5 before radiation sterilization in order to achieve the final desired pH of within the range of between about 6.5-7.6 after sterilization, with a preferred physiological pH being 7.4±0.1. A source of radiation may be Cobalt 60 or by electron beam.

Thixotropic gels of the kind used in the cellular separation of blood as with the assemblies of the invention here are generally described by A. A. Luderer, A. R. Zine, D. M. Hess, J. N. Henyan and G. Odstrchel (Rapid, Quantitative Human Lymphocyte Separation And Purification In A Closed System), *Molecular Immunology*, 16, pp. 621–624 (1979). Also, U.S. Pat. No. 4,190,535 describes suitable thixotropic gels and their preparation and is incorporated herein by reference in its entirety.

Generally, a water insoluble, thixotropic gel chemically inert to blood constituents which can be used in accordance herewith is formulated from a dimethyl-polysiloxane and a precipitated methylated silica in which the methylation renders the material hydrophobic. The thixotropic gel preferably has a specific gravity of within the range of between about 1.055 and 1.080 g/cm$^3$, and most preferably, formed with a specific gravity of about 1.077g/cm$^3$. The ficoll-hypaque used, in this invention may have a specific gravity, for example, of 1.09 g/cm$^3$.

Other objects and advantages of this invention will be apparent from the following description, the accompanying drawings, and the appended claims.

DETAILED DESCRIPTION OF THE INVENTION

Figure 1:
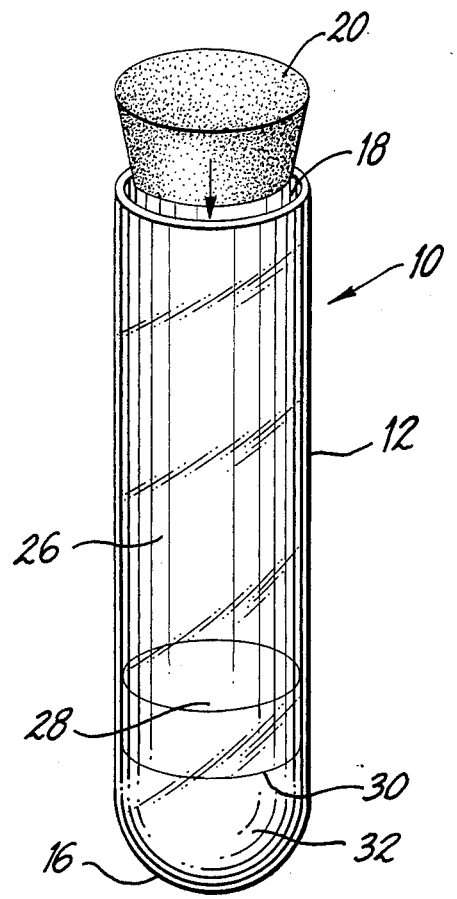
FIG. 1 is a side elevational view of a blood collection assembly illustrating one embodiment of blood collection assembly which may be used with the invention herein.

Referring to the drawing, FIG. 1 illustrates the invention employed as a tube assembly for use in receiving a blood sample which tube assembly is subsequently centrifuged in order to separate the components of the blood sample for subsequent examination.

In FIG. 1, the device 10 includes a tube body 12 with an open end 18 and a closed end 16. The open end, as clearly shown in FIG. 1, includes an elastomeric stopper 20 which serves to close and seal the open end 18 of tube 10. As will be understood by practitioners-in-the-art, prior to use of the assembly 10, the internal cavity 26 of the tube may be evacuated for subsequently causing the ready introduction of a blood sample into tube 12 when a needle is inserted for that purpose through stopper 20.

In order to provide for proper separation of a blood sample introduced into the chamber 26 of tube 12, a ficoll-hypaque density gradient medium 32 is introduced adjacent the closed end of tube 12. The density gradient medium in accordance with this invention may be comprised of ficoll-hypaque, a sucrose-epichlorohydrin polymer with sodium diatrizoate such as HISTOPAQUER ® as discussed above. In accordance with this invention, the ficoll-hypaque solution will have a specific gravity of about 1.09 g/cm$^3$. In addition, it will include a sodium bicarbonate solution containing 0.1-0.5 percent sodium bicarbonate which may be supplemented with a sodium or potassium phosphate (monobasic) solution containing 0.1-0.5 percent sodium or potassium phosphate or any organic buffers in combination with phosphate buffers so as to provide after radiation exposure a pH of at least within the range of between about 6.5 and 7.6. In this connection, after buffering, the ficoll-hypaque needs to be adjusted to an osmolality in the physiological range of between about 250 and 360 mOsm/Kg H$_2$O, and preferably within the range of between about 295 and 330 mOsm/Kg H$_2$O for optimum separation of mononuclear cells.

Referring to FIG. 1, the assembly 10 may include at the surface 30 of the ficoll-hypaque material 32 a thixotropic gel 28 which serves to combine with the buffered ficoll-hypaque to provide an appropriate separation under centrifugal forces of the components of a blood sample subsequently introduced through stopper 20 by insertion of a needle therethrough. The positioning of the gel and the density gradient medium may be reversed depending upon the selection of the gel component. Once assembly 10 has been properly assembled, as discussed above, the assembly may be, in the usual mass production techniques utilized for producing assemblies of the kind discussed herein, exposed in a production line to radiation sterilization. Because of the buffer added to the material, there is no precipitation of the ficoll-hypaque introduced into the assembly during this radiation exposure.

It will be understood that in addition to the components already described above, such assemblies may include anticoagulants for maintaining the blood sample stable prior to examination of the components thereof. For example, EDTA or heparin may be introduced into the assembly, as required.

As purely illustrative of the enhanced results achieved in accordance herewith, one may note the following examples in which comparative ficoll-hypaque-type materials were introduced into a tube assembly as described above and exposed to radiation sterilization for a period of time. In one example, as will be noted, there was no buffer added which resulted in unwanted precipitation of the components of the density gradient medium (which would interfere with subsequent examination of a sample introduced and centrifuged) while in another example in which the buffer was added in accordance with this invention, no precipitation took place. In each example, ten (10) tubes were tested.

EXAMPLE 1

50 ml of HISTOPAQUER ® Brand of ficoll-hypaque having a specific density of 1.09 g/cm$^3$ was introduced into a tube. The HISTOPAQUER ® solution had a pH of 7.07. The solution had no additives included and was exposed to irradiation by Cobalt 60 at the rate of 2.5 megarads. A precipitate developed upon exposure to irradiation, and a subsequent x-ray diffraction study showed no sodium in the resulting solution indicating the sodium diatrizoic acid component of the HISTOPAQUER ® as the precipitate.

EXAMPLE 2

50 ml of HISTOPAQUER ® was introduced into a tube with the HISTOPAQUER ® having a specific gravity of 1.09 g/cm$^3$ in the same manner as in Example 1. Introduced with this HISTOPAQUER ® was a 1 ml portion of sodium hydroxide which was introduced to raise the pH level of the solution to 7.8 before exposure. Of the ten tubes tested with solution as described herein, precipitation was observed in the x-rayed diffractions study in seven tubes.

EXAMPLE 3

In this example 50 ml portions of HISTOPAQUER ® having the same specific gravity 1.09 g/cm$^3$ were introduced into ten sample tubes. Into each tube, 0.1 g of potassium phosphate was introduced to raise the pH to 8.4 in each of the ten tubes. Each of the tubes was exposed to irradiation at the level of 2.5 megarads as in the last two examples and four of the ten tubes showed precipitated material. This indicated that the buffering was inadequate.

EXAMPLE 4

In this example, ten tubes had 50 ml samples of HISTOPAQUER ® introduced into each one followed by 0.1 g of sodium bicarbonate. The pH was raised to 8.1. In all ten tubes, no precipitate was shown. The x-ray diffraction study showed intact molecules of sodium diatrizoate thus indicating why there was no precipitation shown in tubes of this example.

Thus, it can be seen from the above comparative examples that a sucrose/epichlorohydrin polymer with sodium diatrizoate (HISTOPAQUER ®), upon exposure to 1.5-2.5 megarads of Cobalt 60 sterilization precipitated out. By the addition of the appropriate additives, precipitation is eliminated thus making the HISTOPAQUER ® product stable to irradiation in the environment discussed here. The studies indicate that the sodium diatrizoate component of HISTOPAQU- ER ®, upon exposure to irradiation, reverted to free acid form of diatrizoic acid which precipitated in the solution. By buffering the HISTOPAQUER ® with sodium bicarbonate, or other specific buffers in accordance with this invention as discussed above to maintain a specific pH level after irradiation exposure, the acid was not formed and thus no precipitation was observed.

Accordingly, and as will be apparent from the foregoing, there are provided in accordance herewith, methods and compositions for enhancing blood collection assemblies so as to allow for the simpler form of sterilization by exposure to radiation sterilization. Because of this, the relative ease of operation in allowing for radiation sterilization rather than autoclave procedures or filter sterilization, as discussed above, make the objects obtained by the method herein highly advantageous commercially for mass production operations.

While the methods and compositions herein disclosed form preferred embodiments of this invention, this invention is not limited to those specific methods and compositions and changes can be made therein without departing from the scope of the invention which is defined in the appended claims.

What is claimed is:

1. A method for radiation sterilization of blood component separation containers containing ficoll-hypaque, as one of the separation media therefore, while avoiding precipitation of a sodium component of the ficoll-hypaque during exposure to said radiation sterilization, the steps which comprise
   (a) selecting a blood sample separation container for introducing a blood sample therein;
   (b) introducing in a first introducing step at least one blood separation component into said container for providing a blood separation medium for said container,
   said at least one blood separation component including ficoll-hypaque;
   (c) in a second introducing step, introducing into said container a material for adjusting the pH level of said blood separation medium in said container, said material being selected from the group consisting of sodium bicarbonate, sodium bicarbonate with potassium or sodium/mono or dibasic phosphates, sodium carbonate, sodium carbonate with potassium or sodium/mono or dibasic phosphates, tris-hydroxymethyl amino methane with sodium or potassium phosphate, tris-hydroxymethyl amino methane, hydroxyethyl piperazine/N/2/ethane sulfonic acid with sodium or potassium phosphate, and hydroxyethyl piperazine/N/2/ethane sulfonic acid, said material being in an amount sufficient to bring the pH level of said blood separation medium to within the range of between about 6.5 and 7.6 after exposure to radiation sterilization; and
   (d) exposing said container to radiation sterilization.

2. The method of claim 1, wherein said exposing step includes exposure to irradiation by Cobalt 60 at 2.5 megarads.

3. The method of claim 1, wherein said material is sodium bicarbonate with monobasic sodium phosphate, and within the range of between about 0.1 and 0.5% solution of sodium bicarbonate and within the range of between about 0.1 and 0.5% solution of monobasic sodium phosphate.

4. A method as described in claim 1, wherein said container is a tube with a closed end and an open end, said open end sealed by a stopper, and wherein prior to said exposure step, evacuating said container as said stopper is seated in said closed end for sealing said container.

5. A method as described in claim 1, wherein said container is a tube with a closed end and an open end, said open end sealed by a stopper, and wherein after said second introducing step, evacuating said container as said stopper is seated in said closed end for sealing said container.

6. The method of claim 1, wherein said at least one blood separation component further comprises a thixotropic gel.

7. The method of claim 1, wherein said at least one blood separation component further comprises a newtonian gel.

8. The method of claim 1, wherein said at least one blood separation component further comprises an anticoagulant component.

9. A device for separating the components of a blood sample comprising
   a container, said container having disposed therein a blood separation medium, said blood separation medium comprising;
   (a) at least one separation component, said at least one separation component including ficoll-hypaque, and
   (b) a material for adjusting the pH level of said blood separation medium, said material being selected from the group consisting of sodium bicarbonate, sodium bicarbonate with potassium or sodium/mon or dibasic phosphates, sodium carbonate, sodium carbonate with potassium or sodium/mono or dibasic phosphates, tri-hydroxymethyl amion methane with sodium or potassium phosphate,tris-hydroxymethyl amono methan, hydroxyethyl piperazine/N/2/ethane sulfonic acid with sodium or potassium phosphate, and hydroxyethyl piperazine/N/2/ethane sulfonic acid,
   said material being present in said container in an amount sufficient to bring the pH level of said blood separation medium to within the range of between about 6.5 and 7.6 after exposure to sterilizing radiation, whereby precipitation of a sodium component of the ficoll-hypaque during said exposure to said radiation is avoided,
   said device having no blood sample disposed within said container and wherein said container and said blood separation medium have been sterilized by said exposure to said radiation,
   whereby said device may be subsequently used for separation of components of a blood sample by centrifugation.

10. The device of claim 9 wherein said material consists of sodium bicarbonate in an amount within the range of about 0.1 to 0.5% solution and monobasic sodium phosphate in an amount within the range of about 0.1 to 0.5% solution.

* * * * *